(12) United States Patent
Doerr

(10) Patent No.: US 9,867,983 B2
(45) Date of Patent: Jan. 16, 2018

(54) ACTIVE IMPLANTABLE DEVICE SUITABLE FOR USE IN AN MRI SCANNER

(71) Applicant: BIOTRONIK SE & CO. KG, Berlin (DE)

(72) Inventor: Thomas Doerr, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 29 days.

(21) Appl. No.: 14/946,552

(22) Filed: Nov. 19, 2015

(65) Prior Publication Data

US 2016/0151624 A1    Jun. 2, 2016

Related U.S. Application Data

(60) Provisional application No. 62/085,261, filed on Nov. 27, 2014.

(51) Int. Cl.
| | | |
|---|---|---|
| *A61N 1/00* | (2006.01) | |
| *A61N 1/08* | (2006.01) | |
| *A61K 31/201* | (2006.01) | |
| *A61K 31/202* | (2006.01) | |
| *A61K 31/661* | (2006.01) | |
| *A61K 31/685* | (2006.01) | |
| *A61N 1/36* | (2006.01) | |
| *A61N 1/362* | (2006.01) | |
| *A61N 1/37* | (2006.01) | |
| *A61N 1/39* | (2006.01) | |

(52) U.S. Cl.
CPC .............. *A61N 1/08* (2013.01); *A61K 31/201* (2013.01); *A61K 31/202* (2013.01); *A61K 31/661* (2013.01); *A61K 31/685* (2013.01); *A61N 1/3627* (2013.01); *A61N 1/36142* (2013.01); *A61N 1/3718* (2013.01); *A61N 1/3931* (2013.01)

(58) Field of Classification Search
CPC ................................ A61N 1/08; A61N 1/3627
USPC ........................................... 607/5, 63
See application file for complete search history.

(56) References Cited

U.S. PATENT DOCUMENTS

2008/0154342 A1*   6/2008   Digby .................. A61N 1/3718
                                                                            607/63

* cited by examiner

*Primary Examiner* — Nadia A Mahmood
(74) *Attorney, Agent, or Firm* — ARC IP Law, PC; Joseph J. Mayo

(57) ABSTRACT

Embodiments include an implantable device configured to be used in an MRI device, including a control unit, a memory unit, an MRI sensor and a statistics unit. The memory unit includes program information including control programs and/or control parameters that control the function of the control unit, and current state parameters. The MRI sensor is connected to the control unit and responds to a positioning of the implant and/or a patient within or in the immediate vicinity of the MRI device. The statistics unit is connected to the control unit and detects current state parameters present prior to a respective response of the MRI sensor. The control unit selects a control program or control parameters indicated by the state parameters and maintains the control program or control parameters until the MRI sensor indicates a positioning of the implantable device within or in the immediate vicinity of the MRI device.

15 Claims, 4 Drawing Sheets

ACTIVE IMPLANTABLE DEVICE SUITABLE FOR USE IN AN MRI SCANNER

This application claims the benefit of U.S. Provisional Patent Application 62/085,261 filed on 27 Nov. 2014, the specification of which is hereby incorporated herein by reference.

BACKGROUND OF THE INVENTION

Field of the Invention

Embodiments of the invention generally relate to an electronic implantable device configured to be used in an MRI scanner, in particular one or more of an implantable heart therapy device, a heart monitoring device, a cardiac pacemaker and a cardiovertor/defibrillator.

Description of the Related Art

Generally, implantable heart therapy and/or heart monitoring devices include for example heart stimulators in the form of cardiac pacemakers or cardioverters/defibrillators. Such heart stimulators are generally connected to electrode lines, which have stimulation electrodes and optionally additional defibrillation electrodes in a chamber of a heart or in the immediate vicinity thereof. Typically, a cardiac pacemaker may deliver an electric stimulation pulse to the muscle tissue of a heart chamber via a stimulation electrode (more specifically one or more stimulation electrode poles) in order to thus cause a stimulated contraction of the heart chamber, provided the stimulation pulse has a sufficient intensity and the heart muscle tissue (myocardium) is not in a refractory phase at that precise moment. A contraction of a heart chamber stimulated as such may be referred to herein as a stimulated event. A stimulation pulse having sufficient intensity to cause a stimulated contraction of a heart chamber may be referred to herein as "above-threshold". Should a natural contraction of the heart chamber occur, such a contraction may be referred to herein as an autonomous action or as a natural or intrinsic event. A contraction, for example of the right atrium of a heart, may be referred to herein as an atrial event, which for example may be a natural atrial event or, in the case of an atrial cardiac pacemaker, may also be a stimulated atrial event. Generally, natural (intrinsic) and stimulated left-ventricular and right-ventricular events may be distinguished in a similar manner.

Typically, a local excitation of the myocardium spreads, starting from the location of excitation, via stimulus conduction in the myocardium and leads to a depolarization of the muscle cells and therefore to a contraction of the myocardium. Generally, after a short period of time, this causes a repolarization of the muscle cells and therefore a relaxation of the myocardium. Typically, during the phase of depolarization, the heart muscle cells are insensitive to excitation, that is to say are in a refractory state. This time is generally referred to as the refractory period. Typically, the electric potentials accompanying the depolarization and repolarization may be sensed, and the course thereof over time (referred to as an electrocardiogram) may be evaluated.

In an electrocardiogram, generally, action potentials accompanying a contraction of the ventricle and reflecting a depolarization of the heart muscle cells may be identified as a Q-wave, whereas the repolarization of the heart muscle cells accompanying the relaxation of the myocardium is reflected as a T-wave.

In healthy individuals, typically, the respective heart rhythm is determined by the sinus node, which is controlled by the autonomous nervous system. Generally, the sinus node excites the right atrium of a human heart by stimulus conduction and also excites the (right) ventricle of the heart via the atrioventricular (AV) node. Typically, a natural heart rhythm starting from the sinus node may be referred to as the sinus rhythm and leads to natural contractions of the respective heart chamber, which may be detected as natural (intrinsic) events.

Generally, such natural (intrinsic) events are detected by recording the electric potentials of the myocardium of the respective heart chamber with the aid of sensing electrodes, which are part of a corresponding electrode line. Typically, the sensing electrode poles may simultaneously be the stimulation electrode poles and may be used alternately as a stimulation electrode pole and as a sensing electrode pole. Generally, a sensing electrode pole pair, which is formed by two adjacent electrode poles, specifically a point electrode (tip electrode) and a ring electrode, the point electrode also serving as a stimulation electrode pole, is typically provided for the sensing, that is to say the sensing of intrinsic events. Generally, a bipolar recording of an intracardial electrocardiogram (IEGM) is thus provided. Typically, intrinsic events and the stimulation in the ventricle are sensed with the aid of a ventricular electrode line, and the stimulation and the sensing of intrinsic events in the atrium (in the right atrium) are implemented with an atrial electrode line, which electrode lines are connected separately to the respective heart stimulator. In addition, generally, a left-ventricular electrode line may also be provided, which typically protrudes via the coronary sinus and a lateral vein branching off therefrom into the vicinity of the left ventricle, where it may have a small-area stimulation and/or sensing electrode.

Typically, to be able to satisfy the different needs of various patients, implantable heart stimulators may be operated in various operating modes. The various stimulation and sensing modes are generally referred to in a standardized manner using a three-letter code, of which the first letter denotes the location of stimulation (V=ventricle, A=atrium, D=ventricle and atrium), the second letter denotes the location of the sensing (V=ventricle, A=atrium, D=ventricle and atrium), and the third letter denotes the type of operation (I=inhibited, T=triggered, D=both inhibited and triggered). In particular for dual-chamber cardiac pacemakers in DDD mode, generally, a ventricular stimulation may be performed synchronously with an atrial heart rate that is as natural as possible. Typically, should it be impossible to sense any healthy natural heart rate in the atrium, for example in the case of atrial tachycardia or atrial fibrillation, cardiac pacemakers that are atrium-synchronous in principle often have a mode-switching capability in order to switch from an atrium-synchronous ventricular stimulation to an atrium-asynchronous stimulation in VVI mode, should a perceived atrial rate lie outside permissible limits. Generally, ventricular tachycardias within the scope of cardioversion therapy may be treated by stimulation with a stimulation rate above the tachycardia rate.

Typically, the stimulation modes may be set by corresponding control programs, which for example process or ignore detected events, or by control parameters. By way of example, generally, the detection of events in the atrium and/or ventricle may thus be activated or deactivated by a control parameter.

With regard to the references used herein, it is noted that the terms stimulation electrode or sensing electrode within the scope of the invention may include a respective electrode pole on an electrode line, for example the part of an electrode line via which stimulation pulses are delivered or electric potentials are received. It should also be noted that an electrode line used for stimulation may be referred to herein as a "stimulation electrode".

Generally, the sensing electrode poles are connected during operation of the heart stimulator to corresponding sensing units, which may evaluate a respective electrocardiogram recorded via a sensing electrode pole (or a sensing electrode pole pair) and in particular may detect intrinsic atrial or ventricular events, that is to say natural atrial or ventricular contractions. Typically, this is achieved by way of example using a threshold value comparison, wherein an intrinsic event is detected when a respective intracardial electrocardiogram exceeds a threshold value predefined as suitable.

Generally, the respective intrinsic atrial heart rate (atrial frequency) or ventricular heart rate (ventricle frequency) may be derived from the frequency with which atrial or ventricular events follow one another, and for example tachycardias may thus be detected.

Typically, the detection of natural events is additionally used in demand pacemakers to suppress (inhibit) the delivery of stimulation pulses to a corresponding heart chamber should the natural event be detected in a time window prior to the planned delivery of a stimulation pulse to this heart chamber. In the case of rate-adaptive cardiac pacemakers, generally, the moment in time of the delivery of a respective stimulation pulse is planned in accordance with a respective stimulation rate, which is to correspond to the physiological demand of a patient, that is to say for example is higher with greater exertion. Generally, a heart stimulator may be equipped with one or more activity sensors, which for example may be a CLS (closed loop stimulation) sensor.

Typically, it is problematic that the function of such implantable electric medical devices, such as heart stimulators, may be severely adversely affected by strong electromagnetic fields or magnetic fields as occur for example in a magnetic resonance imaging (MRI) scanner (or magnetic resonance scanner or MRI scanner). Generally, many individuals who carry an active implantable medical device (also referred to hereinafter as an implant or IMD) are therefore contraindicated for MRI examinations, although MRI examinations are becoming increasingly important in the field of diagnostic medicine.

In order to still enable MRI examinations for individuals carrying active implantable medical devices, typically, various approaches are used, which are based either on the execution of the MRI examination or on the implantable medical device.

Generally, technologies for identifying magnetic fields are used, which are based on conventional methods for magnetic field detection. For example, United States Patent Application Publication US 2008/0154342, entitled "Implantable Medical Device Comprising Magnetic Field Detector", to Digby et al., appears to describe a method for using a GMR (giant magnetic resistance) sensor in order to detect magnetic fields of MRI devices.

Generally, for example, an implantable cardioverter/defibrillator (ICD) is set by a cardiologist prior to an MRI examination into an operating mode that is not adversely affected by the magnetic fields prevailing in the MRI scanner. Following the MRI examination by a radiologist, typically, a cardiologist has to set the ICD back into an operating mode corresponding to the needs of the patient.

BRIEF SUMMARY OF THE INVENTION

One or more embodiments of the invention improve the suitability of an active implantable medical device, such as under the influence of magnetic fields of a magnetic resonance imaging (MRI) scanner.

At least one embodiment of the invention includes an electronic implantable device that may be used in an MRI scanner, wherein the electronic implantable device includes a control unit and a memory unit. In one or more embodiments, program information including control programs and/or control parameters, which control the function of the control unit, may be stored in the memory unit. In at least one embodiment, current state parameters may be stored, at least temporarily, in the control unit. In one or more embodiments, the electronic implantable device may include an MRI sensor, which is connected to the control unit and which may respond to a positioning of the implant (or of a patient with the implant) within or in the immediate vicinity of an MRI device. In at least one embodiment, the MRI sensor may indicate such a positioning. In one or more embodiments of the invention, the electronic implantable device may include a statistics unit, which is connected to the control unit or is a part thereof. In at least one embodiment, the statistics unit may detect present current state parameters prior to a respective response of the MRI sensor. In one or more embodiments, the control unit may, in response to the MRI sensor's evaluation of the state parameters detected by the statistics unit, select a control program and/or control parameters indicated by the state parameters. In at least one embodiment, the control unit, in response to the MRI sensor's evaluation of the state parameters detected by the statistics unit, may maintain the control program and/or the control parameters until the MRI sensor indicates a positioning of the electronic implantable device within or in the immediate vicinity of the MRI device.

By way of at least one embodiment, the state parameters may include parameters that describe either the operating state of the implantable electronic device or a state of a patient, or both, since the operating state of the implantable electronic device may be dependent on the respective current state of the respective patient. In one or more embodiments, a stimulation rate as a state parameter of the device may be dependent, for example, on a natural rhythm of the patient detected by the implantable device. In at least one embodiment, the natural rhythm may be the rhythm of natural contractions (natural actions, intrinsic events) of a heart chamber.

According to one or more embodiments, the control programs or control parameters may determine the operating mode, such as the respective operating mode of the implantable electronic device, which may be controlled by the control unit. In at least one embodiment, the control programs or control parameters stored in the memory unit may influence the mode of operation of the control unit. In one or more embodiments, the control unit may control the operation of the implantable electronic device, including a delivery of therapy for example, such as the heart stimulation. In one or more embodiments, the control unit may select a control program to be applied or control parameters to be applied, which may define, for example, the delivery of therapy. In at least one embodiment, the selection of a control program to be applied or control parameters to be applied by the control unit may be programmable, for example by storing in the memory unit selection criteria to be applied by the control unit for the selection. In one or more embodiments, the electronic implantable device may be or may include a cardiac pacemaker, wherein the control programs or control parameters may determine for example the sensing and/or stimulation mode of the pacemaker, such as DDD or V00 or A00.

Embodiments of the invention may allow the safe operation of the electronic implant in the MRI scanner, without the need to reprogram or adapt the MRI program immediately before the examination.

Embodiments of the invention include the finding that previously known solutions and a conceivable automatic MRI reprogramming have the disadvantage that, for the MRI switchover, a doctor providing the aftercare for the electronic implant has to store in the implant a program that is tailored to the patient and suitable for the MRI examination. This tailored setting in previously known devices, however, may change over time, such that the doctor is unable to determine thereafter for certain which programming is to be considered safe for a patient in a few months or years to come during an MRI examination.

In at least one embodiment of the invention, the electronic implantable device may be or may include one or more of an implantable pulse generator (IPG), an implantable cardioverter/defibrillator (ICD), a heart stimulator that provides cardial resynchronization therapy (CRT), and a neurostimulator. In one or more embodiments, the electronic implantable device may be or may include one or more of a heart therapy device, a heart monitoring device, an implantable biventricular cardiac pacemaker, and a cardioverter/defibrillator. In at least one embodiment, cardial resynchronization therapy (CRT) may be carried out with a biventricular cardiac pacemaker.

By way of one or more embodiments, the memory unit may contain a control program that may be selected by the control unit, wherein the control program may suppress a triggering of stimulation pulses. In at least one embodiment, the memory unit may contain at least one program that causes an operation mode that is without stimulation.

In one or more embodiments, the implantable electronic device may be or may include a cardiac pacemaker, wherein the memory unit may include a control program or control parameters selectable by the control unit. In at least one embodiment, one or more of the control program and the control parameters may prompt the control unit to cause an asynchronous stimulation in an asynchronous stimulation mode, such as V00 or D00. In one or more embodiments, the electronic implantable device may be or may include a heart stimulator, such as a cardiac pacemaker or ICD. In at least one embodiment, in accordance with the three-letter code described above, the stimulation modes may manage without sensing of intrinsic events, and may not include inhibition or triggering of stimulation pulses by detected intrinsic events. In one or more embodiments, due to alternating magnetic or electromagnetic fields, a heart stimulator may incorrectly detect signals induced by the alternating magnetic or electromagnetic fields as intrinsic events, wherein such incorrectly detected signals are considered by the stimulation modes. In a pure stimulation mode, by way of at least one embodiment, which manages without the detection of intrinsic events, incorrectly detecting signals induced by the alternating magnetic or electromagnetic fields may be absent or avoided.

According to one or more embodiments, the implantable electronic device may be or may include a cardiac pacemaker, wherein the memory unit may store a control program that may be selected by the control unit. In at least one embodiment, the control program may cause an asynchronous stimulation in an asynchronous stimulation mode, such as V00 or D00.

In at least one embodiment, the electronic implantable device may be or may include a heart stimulator, and may include the statistics unit. In one or more embodiments, the statistics unit may include a stimulation trend memory or may be connected to a stimulation trend memory. In at least one embodiment, the statistics unit or the control unit may select a control program to be applied following a response of the MRI sensor, or may select control parameters to be applied following a response of the MRI sensor under consideration of a number of state parameters stored in the stimulation trend memory in a period of time prior to a respective response of the MRI sensor. In one or more embodiments, the stimulation trend memory may include state parameters, which, for example, reflect the delivery of stimulation pulses and/or the frequency of the delivery of stimulation pulses.

According to at least one embodiment, one or more of the statistics unit and the control unit may select a control program to be applied following a response of the MRI sensor or control parameters to be applied following a response of the MRI sensor under consideration of a natural rhythm detected by the heart stimulator in a period of time from a respective response of the MRI sensor. In one or more embodiments, the state parameters influencing the selection of the control program or of the control parameters may include state parameters that describe the state of a patient, as detected by the electronic implantable device.

In at least one embodiment, one or more of the statistics unit and the control unit may select a control program to be applied following a response of the MRI sensor or control parameters to be applied following a response of the MRI sensor under consideration of extrasystoles detected by the heart stimulator in a period of time prior to a respective response of the MRI sensor. In one or more embodiments, one or more of the statistics unit and the control unit may select a respective control program or respective control parameters in accordance with a detected extrasystole trend.

By way of at least one embodiment, irrespective of the type of the electronic implantable device, the memory unit may contain a selection program that controls the selection of a control program to be applied following a response of the MRI sensor, or that controls the selection of control parameters to be applied following a response of the MRI sensor using one or more of the statistics unit and the control unit. In one or more embodiments, the criteria to select the control program or control parameters that are applied by one or more of the statistics unit and the control unit may be programmable. In at least one embodiment, the memory unit may include selection criteria assigned to one or more of the control programs and control parameters. In one or more embodiments, the selection criteria may determine the operating principle of one or more of the control unit and the statistics unit when selecting the respective control program and/or respective control parameters.

In at least one embodiment, the control programs or control parameters to be selected may be selected such that the settings that ensure a fundamentally safe operation of the implantable electronic device in a magnetic resonance scanner, for example, cause the deactivation of the shock delivery in an ICD.

In one or more embodiments, the implantable electronic device may perform test algorithms cyclically in order to regularly automatically update selection criteria for the selection of a control program to be applied following a response of the MRI sensor or control parameters to be applied following a response of the MRI sensor.

By way of at least one embodiment, the implantable electronic device may modify one or more control parameters or one or more control parameters in accordance with detected state parameters. By way of example, in one or more embodiments, a stimulation rate (predefined by corresponding control parameters) to be applied following a response of the MRI sensor may be set or modified by the implantable electronic device such that it is dependent on measured shortest heart cycles (the period between two intrinsic events) and the frequency of extrasystoles. In at least one embodiment, the stimulation rate may be a control parameter that is adapted and thus modified by the state parameters (shortest heart cycles, frequency of extrasystoles) detected by the implantable electronic device.

In one or more embodiments, the MRI sensor may be or may include one or more of a magnetic field sensor, a gradient field sensor, a high-frequency field sensor, a position sensor, a vibration sensor (such as a Lorentz vibration sensor), and a sensor that monitors characteristic voltage profiles, for example in the electrode lines of the implantable medical device.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
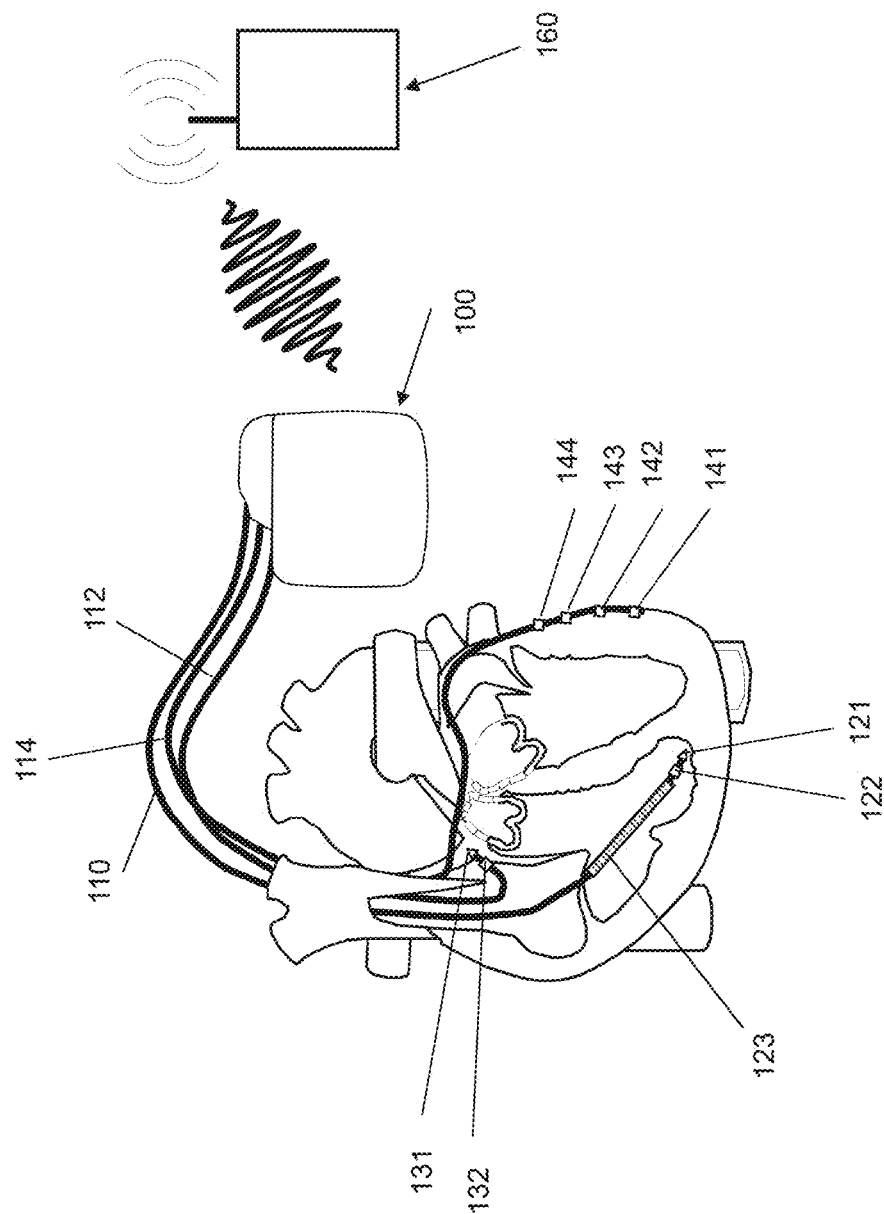
FIG. 1 shows a system with a heart therapy and/or heart monitoring device, as an implantable electronic device, including a three-chamber ICD system.

FIG. 1 shows a heart therapy and/or heart monitoring device and system, including a three-chamber ICD system as an example of an active implantable medical device, according to one or more embodiments of the invention. In at least one embodiment, the implantable medical device may include a generator 100, or a heart stimulator 100, for example as the heart therapy and/or heart monitoring device, connected to a number of implantable electrode lines 110, 112 and 114. One or more embodiments may include a right-ventricular (RV) electrode line 110 that provides right-ventricular sensing and delivers stimulation, which may include a right-ventricular (RV) tip electrode 121 and a right-ventricular (RV) ring electrode 122 at the distal end thereof. During operation, in at least one embodiment, right-ventricular stimulation pulses may be delivered as necessary to deliver biventricular CRT stimulation via the RV tip electrode 121. One or more embodiments may include shock electrodes of coils 123, such as a distal shock coil 123 and/or a proximal shock coil (not illustrated), attached to the RV electrode line 110, to deliver shock. In at least one embodiment, the generator housing of the generator 100 may be a counter electrode.

In one or more embodiments, electrode line 112 may be a right-atrial electrode line 112, which, at the distal end thereof, may include a bipolar sensing and stimulation pole with a right-atrial tip electrode 131 and a right-atrial ring electrode 132. In one or more embodiments, the right-atrial electrode line 112 may sense the atrial rhythm and where necessary applies atrial stimulation.

In at least one embodiment, the system may include a left-ventricular coronary sinus (CS) electrode line to deliver left-ventricular stimulation pulses that provide CRT via one or more of four left-ventricular (CS) stimulation electrode poles 141, 142, 143 and 144.

One or more embodiments may include a wireless bidirectional telemetry unit, for example in the generator 100, to communicate with one or more of external programming devices, control devices, and data transfer devices 160.

Figure 2:
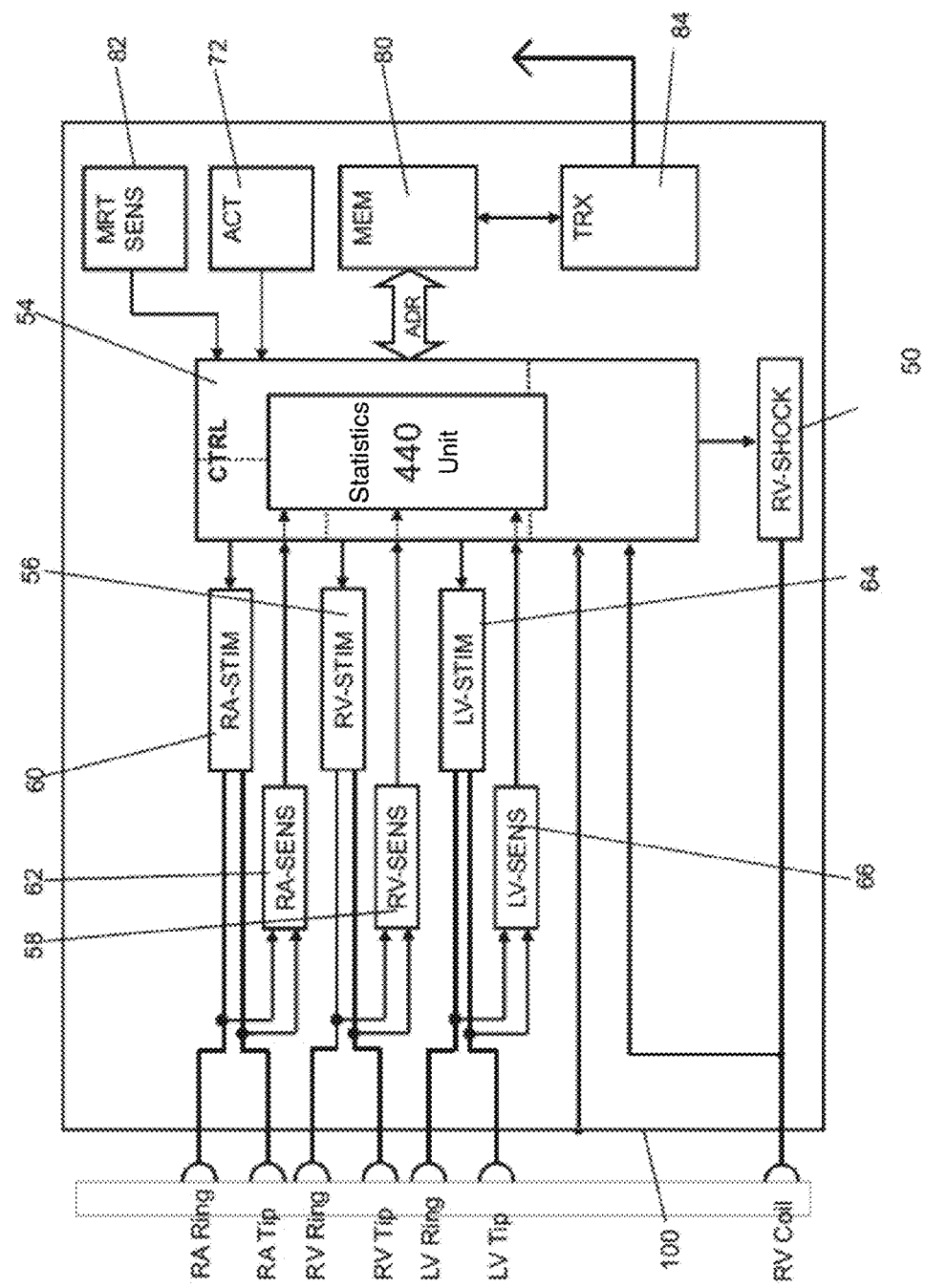
FIG. 2 shows main components of the heart therapy and/or heart monitoring device of FIG. 1.

FIG. 2 shows the main components of the heart stimulator 100 of FIG. 1, according to one or more embodiments of the invention. As shown in FIG. 2, at least one embodiment may include electrical terminals that correspond to the various electrodes 121, 122, 131 and 132, as illustrated on the left-hand side of FIG. 2. In one or more embodiments, the shock electrodes 123 may be connected to a right-ventricular shock pulse generator 50. In at least one embodiment, the shock generator 50 may be connected to a stimulation control unit 54, wherein the stimulation control unit 54 activates the shock pulse generator 50 as required in order to generate and deliver a defibrillation shock.

In one or more embodiments, the terminal of the right-ventricular tip electrode 121 (RV tip) and the connection of the right-ventricular ring electrode 122 (RV ring) may each be connected both to a right-ventricular stimulation unit 56 and to a right-ventricular sensing unit 58. In at least one embodiment, the right-ventricular stimulation unit 56 and the right-ventricular sensing unit 58 may each be connected to the stimulation control unit 54.

By way of one or more embodiments, the right-ventricular stimulation unit 56 may generate a right-ventricular stimulation pulse in response to an actuation signal of the stimulation control unit 54, and may deliver the right-ventricular stimulation pulse via the right-ventricular ring electrode 122 (RV ring) and the right-ventricular tip electrode 121 (RV tip). In at least one embodiment, the housing of the generator 100 may form a neutral electrode, and the right-ventricular stimulation unit 56 may be connected to the terminal of the right-ventricular ring electrode 122 (RV ring) and the housing as another electrode to deliver a stimulation pulse. In one or more embodiments, a right-ventricular stimulation pulse may be distinguished from a defibrillation shock in that the stimulation pulse may include a much lower pulse intensity, such that the stimulation pulse does not excite the entire heart tissue (myocardium) of a heart chamber all at once, compared to a defibrillation shock, but excites the heart muscle cells in the immediate vicinity of the right-ventricular tip electrode (RV tip) 121. In at least one embodiment, the excitation may spread by natural stimulus conduction over the entire right ventricle and may ensure a stimulated contraction of the right ventricle.

In one or more embodiments, the right-ventricular sensing unit 58 may amplify and may filter, initially by an input amplifier, electric potentials applied to the terminal of the right-ventricular ring electrode (RV ring) 122 and the right-ventricular tip electrode (RV tip) 121. In at least one embodiment, the right-ventricular sensing unit 58 may evaluate the profile of the electric signals applied to the inputs of the sensing unit 58, such that the right-ventricular sensing unit 58 may automatically detect a natural (intrinsic)

event, for example an automatic contraction of the right ventricle. In one or more embodiments, such detection may be implemented for example such that the profile of the signal applied to the inputs of the right-ventricular sensing unit 58 is compared with a threshold value. In at least one embodiment, the greatest amplitude of the signal is the R-wave, which defines a natural contraction of the right ventricle, and which may be detected by threshold value comparison. In one or more embodiments, the right-ventricular sensing unit 58 may output a corresponding output signal to the stimulation control unit 54, wherein the output signal indicates a natural contraction of the right ventricle. In at least one embodiment, the moment in time at which the threshold value is exceeded may include the moment of detection for the respective event.

At least one embodiment may include one or more sensing units (not illustrated in FIG. 2) for the shock electrodes. In one or more embodiments, the one or more sensing units may detect signals between the shock electrodes, between the shock electrode 123 and the housing of the generator 100, or between the other shock electrode (the proximal shock electrode or coil) and the housing of the generator 100.

In at least one embodiment, the terminal of the right-atrial point electrode 131 (RA tip) and the terminal of the right-atrial ring electrode 132 (RA ring) may be both connected to a right-atrial stimulation unit 60 and to a right-atrial sensing unit 62, which are each in turn connected to the stimulation control unit 54. In one or more embodiments, the right-atrial stimulation unit 60 may generate stimulation pulses, of which the intensity is sufficient to excite the right-atrial myocardium. In at least one embodiment, the right-atrial stimulation pulses may include a pulse intensity that differs from the right-ventricular stimulation pulses. In one or more embodiments, the right-atrial sensing unit 62 may detect a P-wave from the course of the differential signal applied to the inputs of the sensing unit 62, wherein the P-wave defines a natural (intrinsic) contraction of the right atrium. In at least one embodiment, when the right-atrial sensing unit 62 detects a corresponding P-wave, the right-atrial sensing unit 62 may generate an output signal and may forward the output signal to the stimulation control unit 54, which defines a natural contraction of the right atrium.

By way of one or more embodiments, the terminal of the left-ventricular point electrode 141 (LV tip) and the terminals of the left-ventricular ring electrodes 142, 143 and 144 may be connected in a similar manner to a left-ventricular stimulation unit 64 and a left-ventricular sensing unit 66. In at least one embodiment, the left-ventricular stimulation unit 64 and the left-ventricular sensing unit 66 may be connected to the stimulation control unit 54. In one or more embodiments, the left-ventricular stimulation unit 64 and the left-ventricular sensing unit 66 may function similarly to the stimulation units 56 and 60 and sensing units 58 and 62 as described above.

According to at least one embodiment, the heart stimulator 100 may include an acceleration sensor 72 connected to the stimulation control unit 54, wherein the acceleration sensor 72 may be integrated into the housing of the heart stimulator 100. In one or more embodiments, the acceleration sensor 72 may detect a movement signal dependent on a physical activity of a patient and may output a corresponding first accelerometer output signal to the stimulation control unit 54, indicating the physical activity of the patient. As such, in one or more embodiments, the stimulation control unit 54 may adapt the timing of the stimulation pulse to the need of the patient (hemodynamic need). In at least one embodiment, the accelerometer output signal may be used to determine rest phases, in which a dislocation thereof may be detected.

In one or more embodiments, the generator 100 may include a memory unit 80 connected to the stimulation control unit 54. In at least one embodiment, the memory unit 80 may store signals generated or evaluated by the stimulation control unit 54. In one or more embodiments, the memory unit 80 may store control programs for the stimulation control unit 54, wherein the control programs may be modified.

In at least one embodiment, the stimulation control unit 54 may be connected to an MRI sensor 82. In one or more embodiments, the MRI sensor 82 may be or may include, for example, one or more of a magnetic field sensor, a gradient field sensor, a high-frequency field sensor, a position sensor, a vibration sensor (such as Lorentz vibration sensor), and a sensor that monitors characteristic voltage profiles.

In one or more embodiments, the memory unit 80 may be connected to a telemetry unit 84, wherein the telemetry unit 84 may one or more of wirelessly transfer data stored in the memory unit 80 to the external device 160, transfer program commands from the external device 160 to the heart stimulator 100, and store the transfer program commands in the memory unit 80.

In at least one embodiment, the implantable electronic device may be or may include an electronic implant with an automatic MRI detection and may switchover into a safe state during an MRI examination, wherein at least two patient-tailored MRI program settings may be stored in the implantable electronic device and may be selected automatically in accordance with a patient status detected by the implant prior to the MRI examination.

Figure 3:
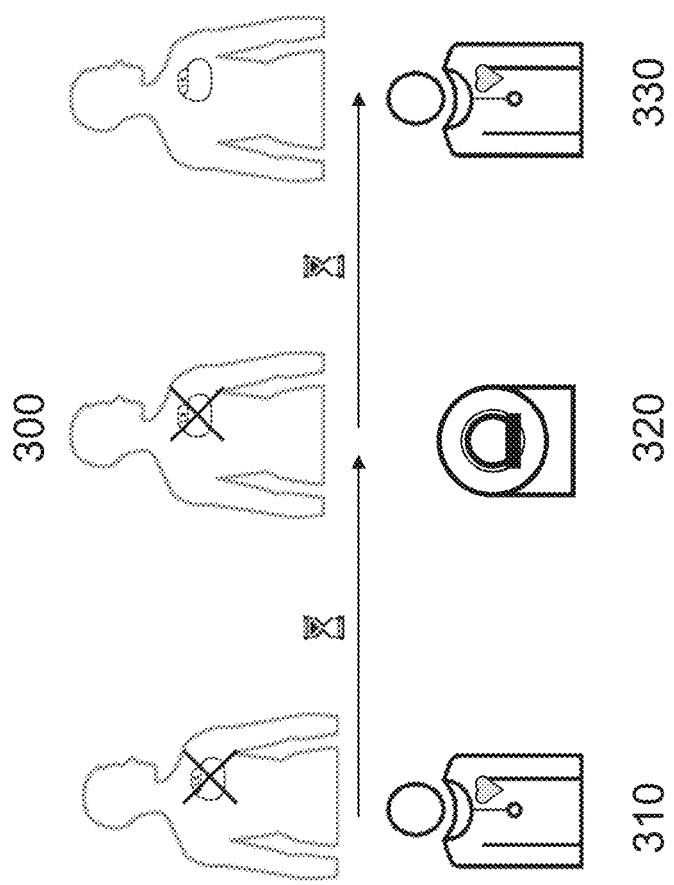
FIG. 3 shows a typical course of an MRI examination of an ICD patient without a device according to one or more embodiments of the invention.

FIG. 3 illustrates a typical course of an MRI examination of an ICD patient without a device according to embodiments of the invention. As shown in FIG. 3, an ICD patient 300 may include an aftercare consultation with a cardiologist 110 before the planned MRI examination, wherein the ICD is switched off. The MRI examination may be carried out by a radiologist 120 after a temporal delay lasting from hours to a few days. After a further delay, the patient may again be treated by the cardiologist 130 and the ICD may be switched back on. During the entire period starting with the MRI examination by a radiologist 120 to the renewed switching-on of the ICD by the cardiologist 130, the patient is without the protection of the implanted defibrillator and may be without rhythm monitoring. The remaining residual risk, for example, which may be measured in proportion to the benefit of the MRI examination, is generally accepted.

By way of one or more embodiments, with the use of an MRI sensor 82, the illustrated sequence of FIG. 3 may be changed such that the MRI setting may now only be effective directly during the MRI examination and the subsequent aftercare by the cardiologist 130 for reprogramming may be spared. Typically, the moment of the first aftercare consultation by the cardiologist 110 in order to determine the MRI program cannot take place arbitrarily prior to the actual MRI examination by the radiologist 120, since the conditions of the patient may change, and therefore an adaptation of the MRI program may be necessary.

Figure 4:
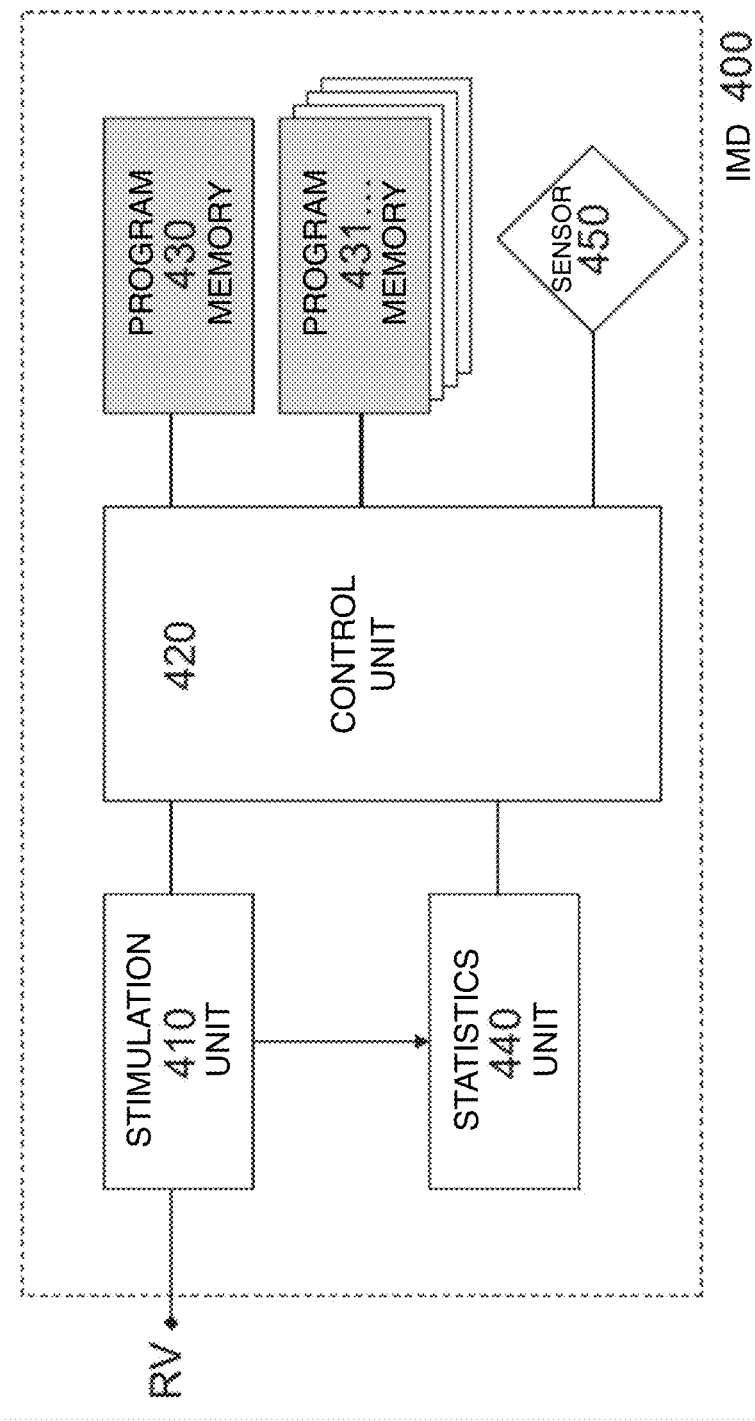
FIG. 4 shows a block diagram of an electronic implantable medical device.

At least one embodiment of the invention provides an anti-bradycardia stimulation. In one or more embodiments, patients who do not require any stimulation may be examined in principle in the OFF mode in the MRI scanner to avoid the risk of arrhythmia induction. In at least one embodiment, patients who require stimulation, however, may be stimulated in an asynchronous operating mode (such as V00, D00) in the MRI scanner. In one or more embodiments, the respective pacemaker dependency may change over the course of time FIG. 4 shows a block diagram, simplified compared to FIG. 1, of an electronic implantable medical device 400, according to one or more embodiments of the invention. In at least one embodiment, the implantable medical device 400 may be connected to a right-ventricular electrode line (RV). In one or more embodiments, the right-ventricular electrode line (RV) may be connected to a sensing and stimulation unit 410 to deliver anti-bradycardia stimulation. During normal operation, by way of at least one embodiment, a control unit 420 may set the stored program initially to deliver need-controlled VVI stimulation. In one or more embodiments, stimulation and sensing statistics may be recorded in a statistics unit 440 in a ring memory, for example recorded for the past 7 days (stimulation component or results of a cyclical natural rhythm test, etc.).

During an MRI examination, in at least one embodiment, the user providing aftercare may use at least two program memories 430 and 431 with a program suitable for the MRI examination. For example, in one or more embodiments, a control program without stimulation (OFF mode) may be stored in the first program memory 430 and a control program with an asynchronous ventricle stimulation (V00 mode) may be stored in the second program memory 431. In at least one embodiment, the program memories 430 and 431 may be memory regions in the memory unit 80 that contain the corresponding control parameters or control programs and may include any selection criteria assigned thereto.

According to one or more embodiments, when the implant identifies an MRI environment using the integrated MRI sensor 450, the control unit 420 may initially evaluate the data of the statistics unit 440 and based on the evaluation may select the most suitable program for the examination (430, 431, . . . ). For example, in at least one embodiment, the OFF mode may be selected from the control program 1 in the program memory 430 if the statistics data cannot identify any stimulation need of the patient, and otherwise the control program 2 in the program memory 431 with V00 mode may be selected.

By way of one or more embodiments of the invention, the system may allow the user to store, once, a number of MRI programs for the respective patient, such that the implant may not need to be checked relatively shortly before the MRI examination.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An electronic implantable device configured to be used in a magnetic resonance imaging (MRI) device, comprising:
a control unit;
a memory unit,
wherein the memory unit stores
program information comprising one or more of control programs and control parameters that control a function of the control unit, and
current state parameters;
an MRI sensor connected to the control unit,
wherein the MRI sensor is configured to
respond to a positioning of the electronic implantable device within or in an immediate vicinity of the MRI device, and
display the positioning; and,
a statistics unit,
wherein the statistics unit is connected to the control unit or is part of the control unit, and
wherein the statistics unit is configured to detect current state parameters present prior to a respective response of the MRI sensor of the current state parameters stored in the memory unit;
wherein the control unit is configured, upon the respective response of the MRI sensor and by evaluation of the current state parameters detected by the statistics unit, to
select one or more of a control program and control parameters indicated of the control programs and control parameters stored in the memory unit by the current state parameters detected, and
maintain the one or more of the control program and the control parameters selected until the MRI sensor indicates the positioning of the electronic implantable device within or in the immediate vicinity of the MRI device; and,
wherein the implantable electronic device is configured to modify one or more of the control parameters or one or more of the control programs in accordance with detected state parameters.

2. The electronic implantable device according to claim 1, wherein the electronic implantable device is one or more of an implantable pulse generator (IPG), an implantable cardioverter/defibrillator (ICD), a heart stimulator configured to provide cardial resynchronization therapy (CRT), and a neurostimulator.

3. The electronic implantable device according to claim 1, wherein the electronic implantable device is a heart stimulator, wherein the control unit selects a control program of the control programs stored in the memory unit such that the control program selected suppresses a triggering of stimulation pulses.

4. The electronic implantable device according to claim 1, wherein the electronic implantable device is a heart stimulator, wherein the control unit selects a control program of the control programs stored in the memory unit such that the control program selected causes an asynchronous stimulation in an asynchronous stimulation mode, wherein the asynchronous stimulation mode comprises V00 or D00.

5. The electronic implantable device according to claim 1, wherein the electronic implantable device is a heart stimulator, and
wherein the statistics unit comprises or is connected to a stimulation trend memory, and
wherein the statistics unit or the control unit is configured to
select a control program of the control programs stored in the memory unit to be applied following the respective response of the MRI sensor, or
select control parameters of the control parameters stored in the memory unit to be applied following the respective response of the MRI sensor
under consideration of a number of state parameters stored in the stimulation trend memory in a period prior to the respective response of the MRI sensor.

6. The electronic implantable device according to claim 5, wherein the stimulation trend memory includes state parameters that reflect one or more of a delivery of stimulation pulses and a frequency of a delivery of stimulation pulses.

7. The electronic implantable device according to claim 1, wherein the electronic implantable device is a heart stimulator, and
wherein one or more of the statistics unit and the control unit is configured to
select a control program of the control programs stored in the memory unit to be applied following the respective response of the MRI sensor, or
select control parameters of the control parameters stored in the memory unit to be applied following the respective response of the MRI sensor
under consideration of a natural rhythm detected by the heart stimulator in a period of time prior to the respective response of the MRI sensor.

8. The electronic implantable device according to claim 1, wherein the electronic implantable device is a heart stimulator, and
wherein one or more of the statistics unit and the control unit are configured to
select a control program of the control programs stored in the memory unit to be applied following the respective response of the MRI sensor, or
select control parameters of the control parameters stored in the memory unit to be applied following the respective response of the MRI sensor
under consideration of extrasystoles detected by the heart stimulator in a period of time prior to the respective response of the MRI sensor.

9. The electronic implantable device according to claim 1, wherein the memory unit comprises a selection program that controls a selection of a control program of the control programs stored in the memory unit to be applied following the respective response of the MRI sensor or selection of control parameters of the control parameters stored in the memory unit to be applied following the respective response of the MRI sensor via one or more of the statistics unit and the control unit.

10. The electronic implantable device according to claim 9, wherein the memory unit further comprises selection criteria assigned to one or more of the control programs and the control parameters, wherein the selection criteria determine an operating principle of the control unit or of the statistics unit when selecting the control program or the control parameters.

11. The electronic implantable device according to claim 1, wherein the implantable electronic device is configured to carry out cyclical test algorithms to regularly and automatically update selection criteria to select a control program of the control programs stored in the memory unit to be applied following the respective response of the MRI sensor or to select control parameters of the control parameters stored in the memory unit to be applied following the respective response of the MRI sensor.

12. The electronic implantable device according to claim 1, wherein the MRI sensor is one or more of a magnetic field sensor, a gradient field sensor, a high-frequency field sensor, a position sensor, a vibration sensor, and a sensor that monitors characteristic voltage profiles.

13. An electronic implantable device configured to be used in a magnetic resonance imaging (MRI) device, comprising:
a control unit;
a memory unit,
wherein the memory unit stores
program information comprising one or more of control programs and control parameters that control a function of the control unit, and
current state parameters;
an MRI sensor connected to the control unit,
wherein the MRI sensor is configured to
respond to a positioning of the electronic implantable device within or in an immediate vicinity of the MRI device, and
display the positioning; and,
a statistics unit,
wherein the statistics unit is connected to the control unit or is part of the control unit, and
wherein the statistics unit is configured to detect current state parameters present prior to a respective response of the MRI sensor of the current state parameters stored in the memory unit;
wherein the control unit is configured, upon the respective response of the MRI sensor and by evaluation of the current state parameters detected by the statistics unit, to
select one or more of a control program and control parameters indicated of the control programs and control parameters stored in the memory unit by the current state parameters detected, and
maintain the one or more of the control program and the control parameters selected until the MRI sensor indicates the positioning of the electronic implantable device within or in the immediate vicinity of the MRI device; and,
wherein the implantable electronic device is configured to carry out cyclical test algorithms to regularly and automatically update selection criteria to select a control program of the control programs stored in the memory unit to be applied following the respective response of the MRI sensor or to select control parameters of the control parameters stored in the memory unit to be applied following the respective response of the MRI sensor.

14. An electronic implantable device configured to be used in a magnetic resonance imaging (MRI) device, comprising:
a control unit;
a memory unit,
wherein the memory unit stores
program information comprising one or more of control programs and control parameters that control a function of the control unit, and
current state parameters;
an MRI sensor connected to the control unit,
wherein the MRI sensor is configured to
respond to a positioning of the electronic implantable device within or in an immediate vicinity of the MRI device, and
display the positioning; and,
a statistics unit,
wherein the statistics unit is connected to the control unit or is part of the control unit, and
wherein the statistics unit is configured to detect current state parameters present prior to a respective response of the MRI sensor of the current state parameters stored in the memory unit;
wherein the control unit is configured, upon the respective response of the MRI sensor and by evaluation of the current state parameters detected by the statistics unit, to select one or more of a control program and control parameters indicated of the control programs and control parameters stored in the memory unit by the current state parameters detected, and maintain the one or more of the control program and the control parameters selected until the MRI sensor indicates the positioning of the electronic implantable device within or in the immediate vicinity of the MRI device; and, wherein the electronic implantable device is a heart stimulator, and wherein one or more of the statistics unit and the control unit is configured to select a control program of the control programs stored in the memory unit to be applied following the respective response of the MRI sensor, or select control parameters of the control parameters stored in the memory unit to be applied following the respective response of the MRI sensor under consideration of a natural rhythm detected by the heart stimulator in a period of time prior to the respective response of the MRI sensor.

15. An electronic implantable device configured to be used in a magnetic resonance imaging (MRI) device, comprising:

a control unit;

a memory unit, wherein the memory unit stores program information comprising one or more of control programs and control parameters that control a function of the control unit, and current state parameters;

an MRI sensor connected to the control unit, wherein the MRI sensor is configured to respond to a positioning of the electronic implantable device within or in an immediate vicinity of the MRI device, and display the positioning; and, a statistics unit, wherein the statistics unit is connected to the control unit or is part of the control unit, and wherein the statistics unit is configured to detect current state parameters present prior to a respective response of the MRI sensor of the current state parameters stored in the memory unit;

wherein the control unit is configured, upon the respective response of the MRI sensor and by evaluation of the current state parameters detected by the statistics unit, to select one or more of a control program and control parameters indicated of the control programs and control parameters stored in the memory unit by the current state parameters detected, and maintain the one or more of the control program and the control parameters selected until the MRI sensor indicates the positioning of the electronic implantable device within or in the immediate vicinity of the MRI device; and, wherein the electronic implantable device is a heart stimulator, and wherein one or more of the statistics unit and the control unit are configured to select a control program of the control programs stored in the memory unit to be applied following the respective response of the MRI sensor, or select control parameters of the control parameters stored in the memory unit to be applied following the respective response of the MRI sensor under consideration of extrasystoles detected by the heart stimulator in a period of time prior to the respective response of the MRI sensor.

* * * * *